United States Patent [19]
Iddan et al.

[11] Patent Number: 5,604,531
[45] Date of Patent: Feb. 18, 1997

[54] IN VIVO VIDEO CAMERA SYSTEM

[75] Inventors: Gavriel J. Iddan, Haifa; Doron Sturlesi, Timrat, both of Israel

[73] Assignee: State of Israel, Ministry of Defense, Armament Development Authority, Rafael, Israel

[21] Appl. No.: 374,272

[22] Filed: Jan. 17, 1995

[30] Foreign Application Priority Data

Jan. 17, 1994 [IL] Israel ........................................ 108352

[51] Int. Cl.$^6$ .............................. H04N 7/18; A61B 1/04; A61B 1/06
[52] U.S. Cl. ................... 348/76; 455/66; 455/95; 455/100; 600/109
[58] Field of Search ..................... 348/65, 76; 455/66, 455/95, 100; 600/109; H04N 7/18

[56] References Cited

U.S. PATENT DOCUMENTS

| | | | |
|---|---|---|---|
| 4,278,077 | 7/1981 | Mizumoto | 600/109 |
| 5,267,033 | 11/1993 | Hoshino | 455/95 |

FOREIGN PATENT DOCUMENTS

| | | |
|---|---|---|
| 2929429A1 | 2/1980 | Germany. |
| 3440177A1 | 5/1986 | Germany. |

OTHER PUBLICATIONS

Rowlands et al., "The Radio Pill: Telemetering from the Digestive Tract", *British Communications and Electronics*, Aug. 1960, pp. 598–601.
Yarbrough, III et al., "Evaluation of the Heidelberg pH Capsule: Method of Tubeless Gastric Analysis", *The American Journal of Surgery*, vol. 117, Feb. 1969, pp. 185–192.
*Bio–Medical Telemetry: Sensing and Transmitting Biological Information from Animals and Man*, R. Stuart Mackay, John Wiley and Sons, New York, 1970, pp. 244–245.
*Manual of Photogrammetry*, vol. 1., Third Edition, American Society of Photogrammetry, 1966, pp. 812–813.
H. Lange et al. "Heidelberger Kapsel—ein Kleinstsender fur die pH–Messung im Magen". Telefunk–Zeitung, vol. 36, No. 5, 1963, pp. 265–270.

*Primary Examiner*—Howard W. Britton
*Attorney, Agent, or Firm*—Skjervan, Morrill, MacPherson, Franklin & Friel; Forrest E. Gunnison

[57] ABSTRACT

An in vivo video camera system and an autonomous video endoscope are described. Each system includes a swallowable capsule, a transmitter and a reception system. The swallowable capsule includes a camera system and an optical system for imaging an area of interest onto the camera system. The transmitter transmits the video output of the camera system and the reception system receives the transmitted video output.

17 Claims, 8 Drawing Sheets

IN VIVO VIDEO CAMERA SYSTEM

FIELD OF THE INVENTION

The present invention relates to in vivo measurement systems such as for the digestive system in general and in vivo video camera systems in particular.

BACKGROUND OF THE INVENTION

Various in vivo measurement systems are known in the art. They typically include swallowable electronic capsules which collect data and which transmit the data to a receiver system. These intestinal capsules, which are moved through the digestive system through the action of digestion, are often called "Heidelberg" capsules and are utilized to measure pH, temperature and pressure throughout the intestines. They have also been utilized to measure gastric residence time, which is the time it takes for food to pass through the stomach and intestines.

The intestinal capsules typically include a measuring system and a transmission system, where the transmission system transmits the measured data at radio frequencies to the receiver system.

The following articles describe swallowable electronic capsules:

E. N. Rowland and H. S. Wolff, "The Radio Pill: Telemetering from the Digestive Tract", *British Communications and Electronics,* August 1960, pp. 598–601; and Yarborough, D. R. III, et al., "Evaluation of the Heidelberg Capsule: Method of Tubeless Gastric Analysis", *The American Journal of Surgery,* Vol. 117, February 1969, pp. 185–191.

Other in vivo measuring systems are endoscopes, long tubes which the patient swallows. These are often utilized to provide images of the upper or lower gastro-intestinal tract. However, because they are not very flexible, they do not move easily through small intestines, and thus, they do not provide views of the small intestines.

There are currently two types of endoscopes. Fiber-optic endoscopes utilize a fiber optic waveguide to transmit the video signal from the area of interest to the electronics located outside the patient's body. Video endoscopes place an electronic camera at the area of interest and store the images until after the test finishes.

SUMMARY OF THE PRESENT INVENTION

It is an object of the present invention to provide a tubeless in vivo video camera system. Such a system includes a capsule which can pass through the entire digestive tract and thus, operates as an autonomous video endoscope.

There is therefore provided, in accordance with a preferred embodiment of the present invention, an in vivo video camera system including a swallowable capsule and a reception system. The capsule includes a) a camera system, b) an optical system for imaging an area of interest onto the camera system and c) a transmitter which transmits the video output of the camera system.

Additionally, in accordance with a preferred embodiment of the present invention, the reception system receives the transmitted video output and includes a) an antenna array capable of surrounding a body for receiving the transmitted video output and for producing a plurality of received signals and b) a demodulator capable of transforming the plurality of received video signals into a single video datastream.

Moreover, in accordance with a preferred embodiment of the present invention, the system includes a data processing system which generates tracking and video data from the single datastream. Optionally, the system can also include apparatus for operating the transmitter intermittently.

Moreover, in accordance with a preferred embodiment of the present invention, the optical system includes a viewing window located along one side of the swallowable capsule.

In accordance with an alternative embodiment of the present invention, the optical system includes an axicon optical element and a relay unit. The axicon optical element has a conical outer surface which, when the conical outer surface is in contact with inner walls of a flexible tube (such as the digestive tract), creates a conical object on the conical outer surface. The axicon optical element compensates for the conical shape of the conical object. The relay unit relays the compensated object to the camara system.

Moreover, in accordance with the alternative preferred embodiment of the present invention, the axicon optical element has an axis of symmetry and a borehole centered around the axis of symmetry.

Additionally, in accordance with the alternative preferred embodiment of the present invention, the optical system includes a light source located within said borehole of the axicon optical element.

Finally, in accordance with the alternative preferred embodiment of the present invention, the axicon element is located before the relay unit and the camera system thereby to enter said flexible tube first and to open up the flexible tube if it has collapsed.

BRIEF DESCRIPTION OF THE DRAWINGS

The present invention will be understood and appreciated more fully from the following detailed description taken in conjunction with the drawings in which:

FIGS. 7 and 8 are schematic illustration of calculations performed by a data processor, wherein FIG. 6 is a top view illustration of the antenna array and FIG. 7 is a cross-sectional illustration of the antenna array;

DETAILED DESCRIPTION OF PREFERRED EMBODIMENTS

Figure 1:
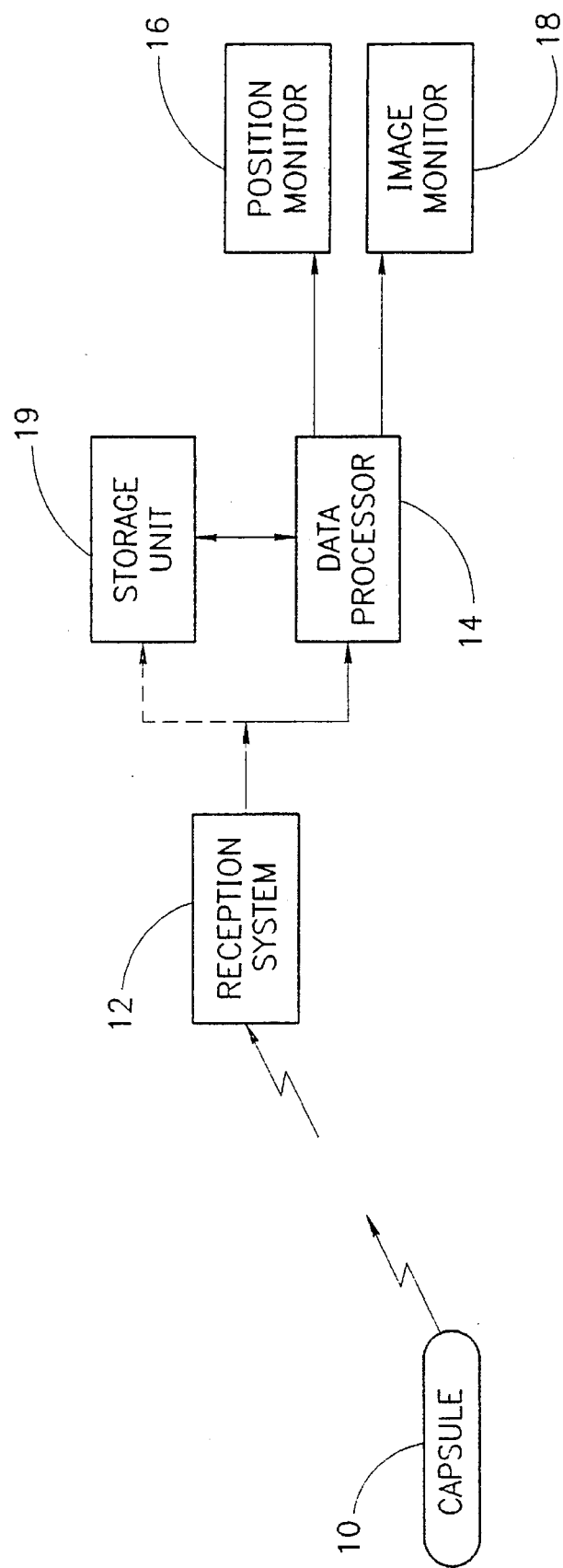
FIG. 1 is a block diagram illustration of an in vivo video camera system, constructed and operative in accordance with a first preferred embodiment of the present invention.

Reference is now briefly made to FIG. 1 which illustrates, in block diagram format, an in vivo video camera system, constructed and operative in accordance with preferred embodiments of the present invention.

The in vivo video camera system typically comprises a swallowable capsule 10 for viewing inside the digestive system and for transmitting at least video data, a reception system 12 typically located outside a patient, and a data processor 14 for processing the video data. The data processor 14 typically operates two monitors, a position monitor 16 on which the current location of the capsule 10 within the digestive system is displayed and an image monitor 18 on which the image currently viewed by the capsule 10 is displayed.

The reception system 12 can either be portable, in which case, the data it receives is temporarily stored in a storage unit 19 prior to its processing in data processor 14, or it can be stationary and close to the data processor 14.

Figure 2:
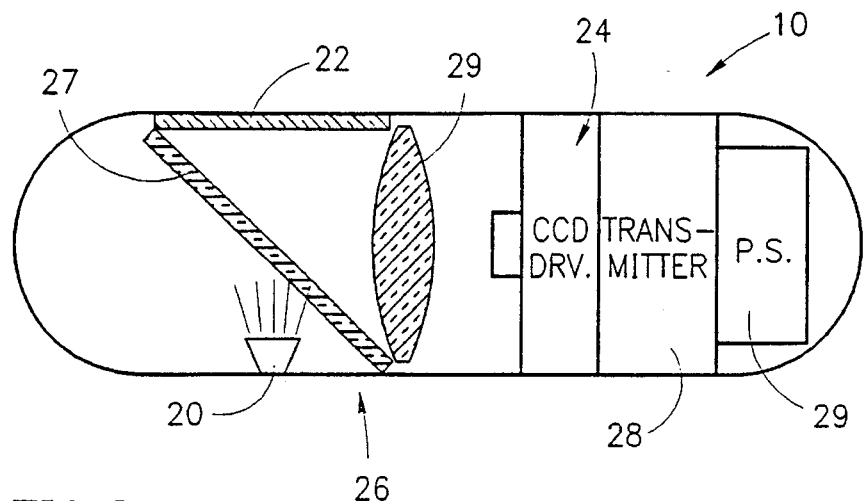
FIG. 2 is a schematic illustration of a video camera capsule forming part of the system of FIG. 1.
Figure 3A:
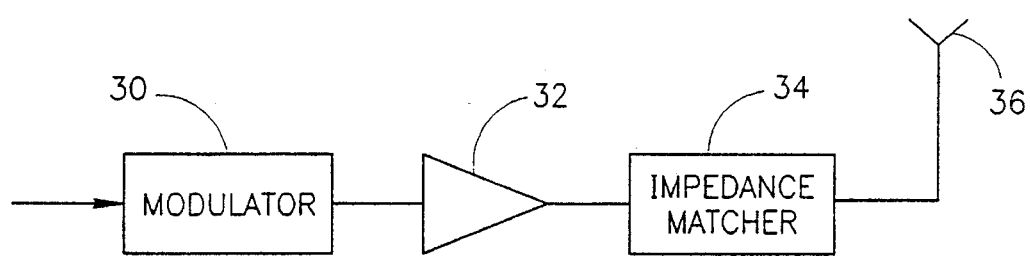
FIG. 3A is a schematic illustration of a transmitter forming part of the capsule of FIG. 2.
Figure 3B:
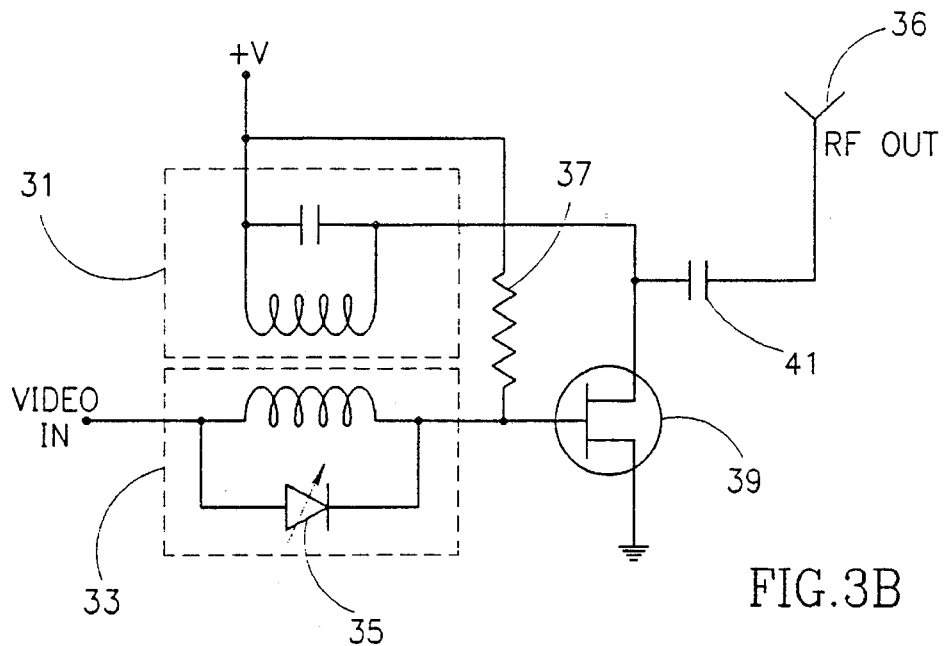
FIG. 3B is a circuit diagram illustration of the transmitter of FIG. 3A.

Reference is now made to FIGS. 2, 3A and 3B which illustrate the capsule and its elements. The capsule 10 typically comprises a light source 20 (FIG. 2), a viewing window 22 through which the light illuminates the inner portions of the digestive system, a camera system 24, such as a charge-coupled device (CCD) camera, which detects the images, an optical system 26 which focusses the images onto the CCD camera system 24, a transmitter 28 which transmits the video signal of the CCD camera system 24 and a power source 29, such as a battery, which provides power to the entirety of electrical elements of the capsule.

The capsule can additionally include sensor elements for measuring pH, temperature, pressure, etc. These sensor elements are described in the prior art.

A suitable small CCD camera system 24 is the 0.25" color CCD cameras of Sony Corporation of Japan. This single chip includes the CCD device and the electronics for producing a video signal from the output of the CCD device. The CCD device can either provide black and white signals or color signals.

Because it is desired to view the walls of the digestive tract, the viewing window 22 typically is located on a side 23 of the capsule 10. Accordingly, the optical system 26 typically comprises a mirror 27 and a focussing lens 29. The mirror 27 is a dichroic mirror which transmits the light from the light source 20, such as a light emitting diode, to the walls of the digestive tract via the viewing window 22. Mirror 27 also deflects the light reflected from the digestive system towards the lens 29. Lens 29 then focusses the light onto the CCD camera system 24.

A suitable transmitter 28 is illustrated in FIG. 3A. It comprises a modulator 30 receiving the video signal from the CCD camera 24, a radio frequency (RF) amplifier 32, an impedance matcher 34 and an antenna 36. The modulator 30 converts the input video signal having a cutoff frequency $f_c$ of less than 5 MHz to an RF signal having a carrier frequency $f_r$, typically in the range of 1 GHz. After amplification by amplifier 32, the RF signal has a bandwidth of ft. The impedance marcher 34 increases the impedance of the circuit to match that of the antenna 36.

FIG. 3B illustrates one possible implementation of the transmitter 28 producing less than 1 milliwatt of power. Other implementations are also included in the scope of the present invention.

The transmitter of FIG. 3B comprises two coupled oscillator tanks 31 and 33, each formed of an inductor and a capacitor, wherein oscillator tank 33 includes a variable capacitor 35. Additionally, the transmitter 28 comprises a voltage divider 37, a transistor 39 and an impedance matching capacitor 41.

The two oscillator tanks 31 are connected in a regeneration loop via transistor 39. The voltage divider 37 typically divides the input voltage, typically of 3 V.

It is noted that the capsule is moved through the digestive tract via the peristaltic motion of the digestive muscles. Since the focal plane of the optical system 26 is fixed close to the housing of the capsule 10, only body parts located close by can be viewed. Thus, the capsule is typically effective only within the small and large intestines.

For example, in the small intestines, the muscles squeeze only when food (or the capsule 10) passes them by. The capsule 10 can optionally be designed to collect images only when the muscles are squeezing. This saves battery power, but requires either a sensor, such as a pressure sensor, or a duty cycle based on the expected operation of the muscles.

Figure 4:
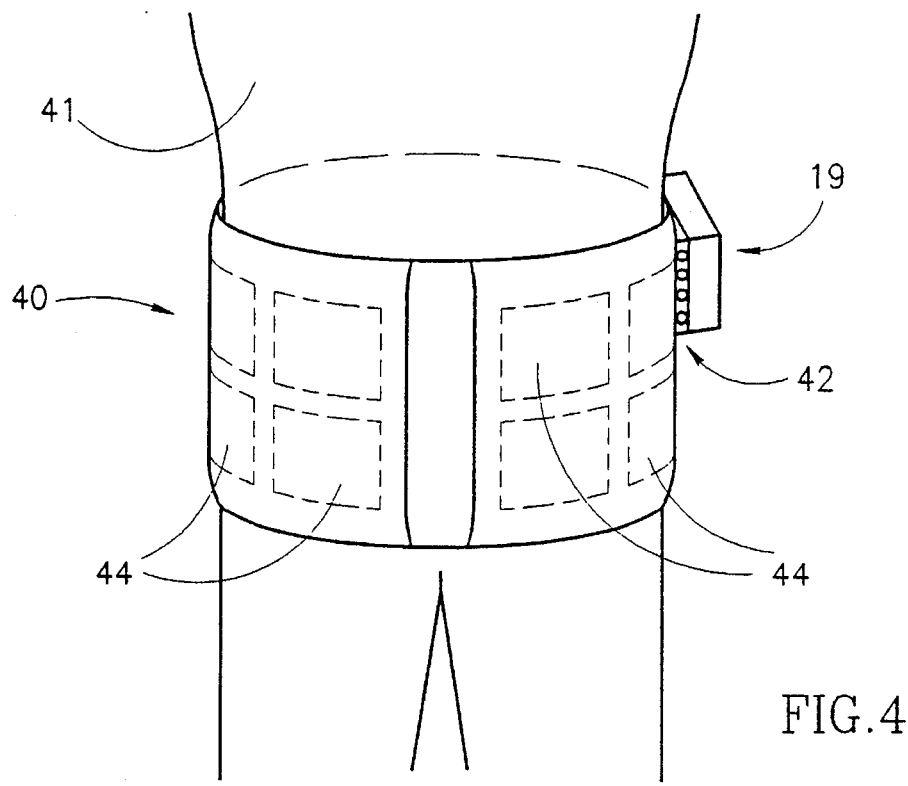
FIG. 4 is a pictorial illustration of a portable reception system forming part of the system of FIG. 1.
Figure 5:
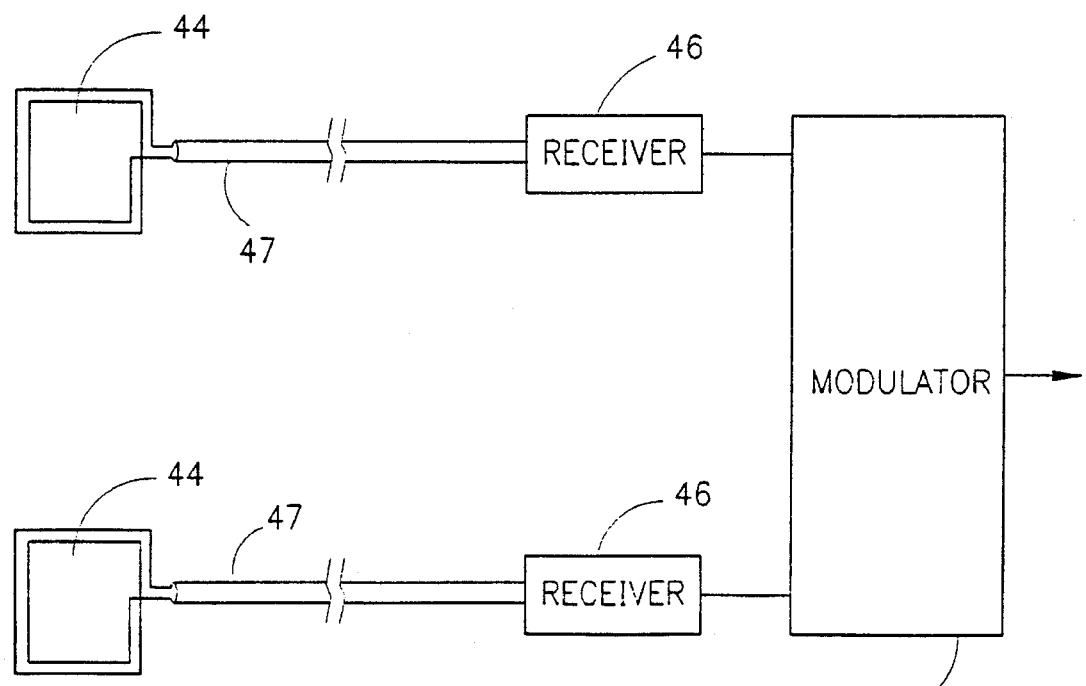
FIG. 5 is a schematic illustration of a reception system forming part of the system of FIG. 1.

Reference is now made to FIGS. 4 and 5 which illustrate a portable embodiment of the reception system 12. The reception system 12 typically comprises an antenna array 40, wrapped around the central portion of a trunk 41 of the patient, and a signal sampler 42.

The antenna array 40 typically comprises a multiplicity of antennas 44, each formed of a rectangular or circular coil of wire, held within a suitably insulating material, such as cloth or plastic. In the exemplary embodiment illustrated in FIG. 4, there are shown 16 antennas 42, formed into two rows of eight antennas 42 each. Fewer or more antennas can be utilized as long as they are located so as to be able to determine from their output the location of the capsule 10 within the body of the patient.

The signal sampler 42 typically comprises a multiplicity of receivers 46 (FIG. 3), one for each antenna 44 and connected thereto with a thin coaxial cable 47, and a multiplexer 48. The receivers 46 decipher the data provided by their corresponding antennas 44. The multiplexer 48 continually scans the output of the receivers 46, providing the combined antenna data as a single output signal.

A suitable receiver 46 must be capable of detecting a signal having the carrier frequency $f_r$ and the bandwidth $f_c$ described hereinabove. Such a receiver can be similar to those found in televisions or it can be one similar to those described on pages 244–245 of the book *Biomedical Telemetry* by R. Stewart McKay and published by John Wiley and Sons, 1970.

As the capsule 10 moves through the digestive system, it views walls of the digestive system and transmits the resultant images to the reception system 12. The reception system 12 receives a multiplicity of versions of the images, each version received by a different antenna 44, and either stores the received signals in the storage unit 19 or provides the received signals to the data processor 14.

From the multiplicity of versions of the images, the position of the capsule 10 within the trunk 41 can be determined and the signal from the antenna 44 closest to the capsule 10 at any given time chosen as the current video source.

Figure 6:
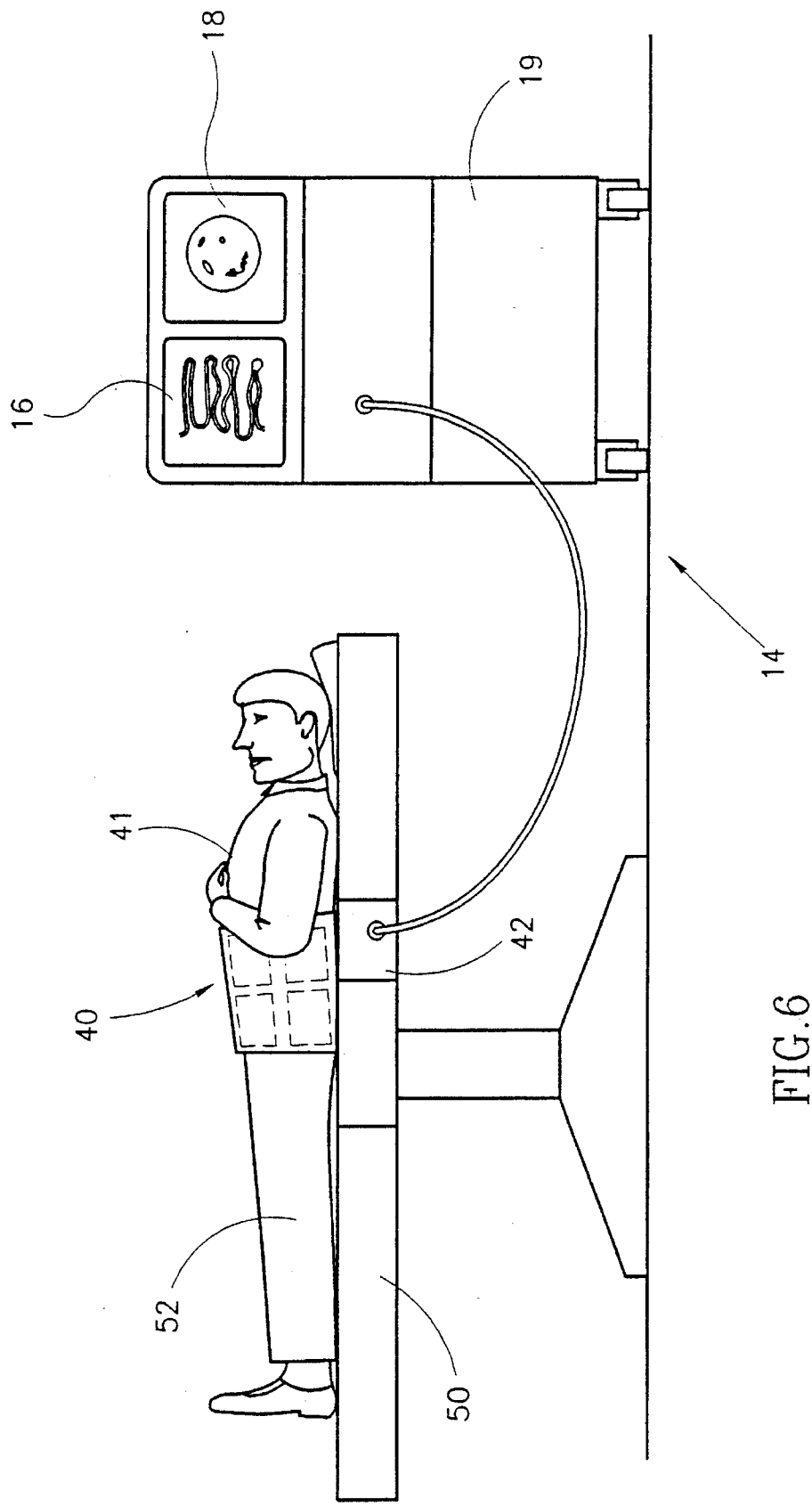
FIG. 6 is a pictorial illustration of an alternative embodiment of the present invention having a stationary reception system.

Reference is now made to FIG. 6 which illustrates a stationary in vivo video camera system. In this alternative embodiment, the antenna array 40 and sampler 42 are affixed to a table 50 on which a patient 52 lies. As in the previous embodiment, the antenna array 40 surrounds the central portion of the patient's trunk 41.

In this alternative embodiment, the output of sampler 42 is provided directly to data processor 14 which then outputs its results on position monitor 16 and image monitor 18, wherein the position monitor 16 typically displays the present and past locations of the capsule 10 within the digestive system and the image monitor 18 typically displays the image viewed by the capsule 10 when at the final location marked on position monitor 16. The output of the data processor 14, as well as of the reception system 12, can also be stored in storage unit 19.

The operation of processing unit 14 will now be described with reference to FIGS. 7 and 8.

The data processor 14 determines the image to be provided on image monitor 18 by continually determining which antenna 44 provides the strongest signal. To do so, the data processor 14 first separates the signal from the reception system 12 into the components from each antenna 44, determines the amount of power in the signals of each antenna 44 and then selects the one with the highest power.

To determine the location of the capsule 10, the data processor 14 first separates the signal from the reception system 12 into the components from each antenna 44. It then determines the location of the capsule 10 by comparing the output of certain ones of the antennas FIG. 7 is a front view illustration of the patient 52 with the antenna array 40 wrapped around him. On it four antennas 44a–44d are noted. Antennas 44a and 44b are located in a column at one side of the patient 52 and antennas 44c and 44d are located in a column at the other side of the patient 52.

Since the strength of a signal received by any given antenna depends on its distance from and angle to the transmitter, the ratio of the signal strengths between any two antennas which have the transmitter between them is constant along a curve which intersects the location of the transmitter. Thus, antennas 44a and 44b define curve 60a and antennas 44c and 44d define curve 60b.

The intersection of curves 60a and 60b is the location of the transmitter which is the location of the capsule 10. The curves 60a and 60b are typically determined in a calibration step for a predefined number of constant values.

The designation of antennas 44a–44d depends on and is determined from the width $L_1$ of the patient 52, which value is typically provided to data processor 14. Alternatively, there can be a plurality of antenna arrays 40, one for each of a pre-defined number of widths $L_1$. The antennas 44a–44d are then constant for each antenna array 40.

The location of the capsule 10 thus generated is typically denoted by a two-dimensional vector P, having a length P and an angle θ, from the center point O of an X-Y coordinate system.

Figure 7:
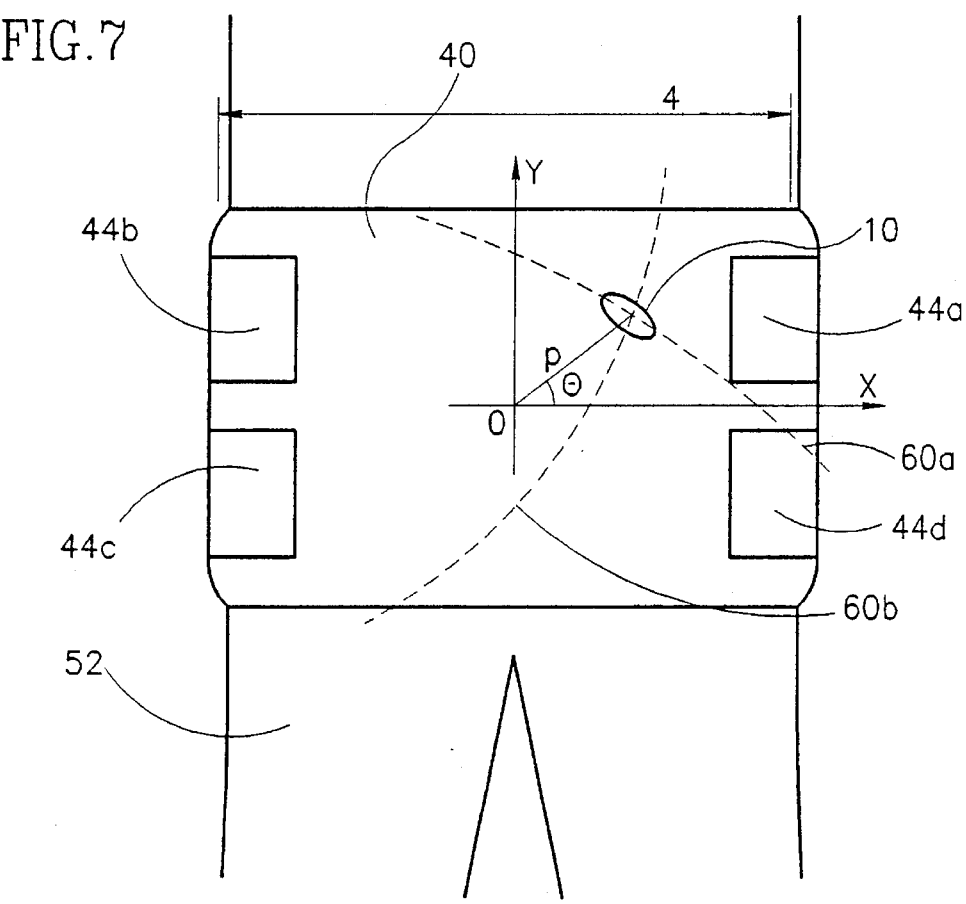
Figure 8:
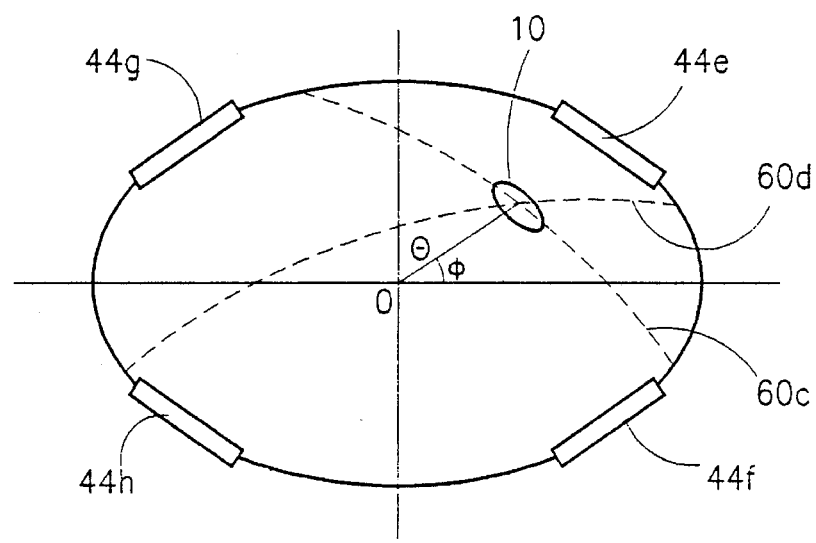

The cross-sectional location (within an X-Z plane) of the capsule 10 can also be determined using a similar calculation to that illustrated in FIG. 7. A cross-section of the patient 52 is illustrated in FIG. 8. For this determination, four antennas 44e–44h, which are opposite in a cross-sectional manner, are utilized.

Once again, the ratio of the signal strengths between two antennas which have the transmitter between them is constant along a curve which intersects the location of the transmitter. Thus, antennas 44e and 44h define curve 60c and antennas 44f and 44g define curve 60d.

The location of the capsule 10 thus generated is typically denoted by a two-dimensional vector Q having a length Q and an angle φ, from the center point 0.

The two vectors P and Q are combined to determine the three-dimensional location of the capsule 10. The location can be displayed two- or three-dimensionally on position monitor 16, typically, though not necessarily, as an overlay to a drawing of the digestive tract.

It will be appreciated that other methods of determining the location of the capsule 10 can alternatively be utilized, as can other reception systems.

Figure 9:
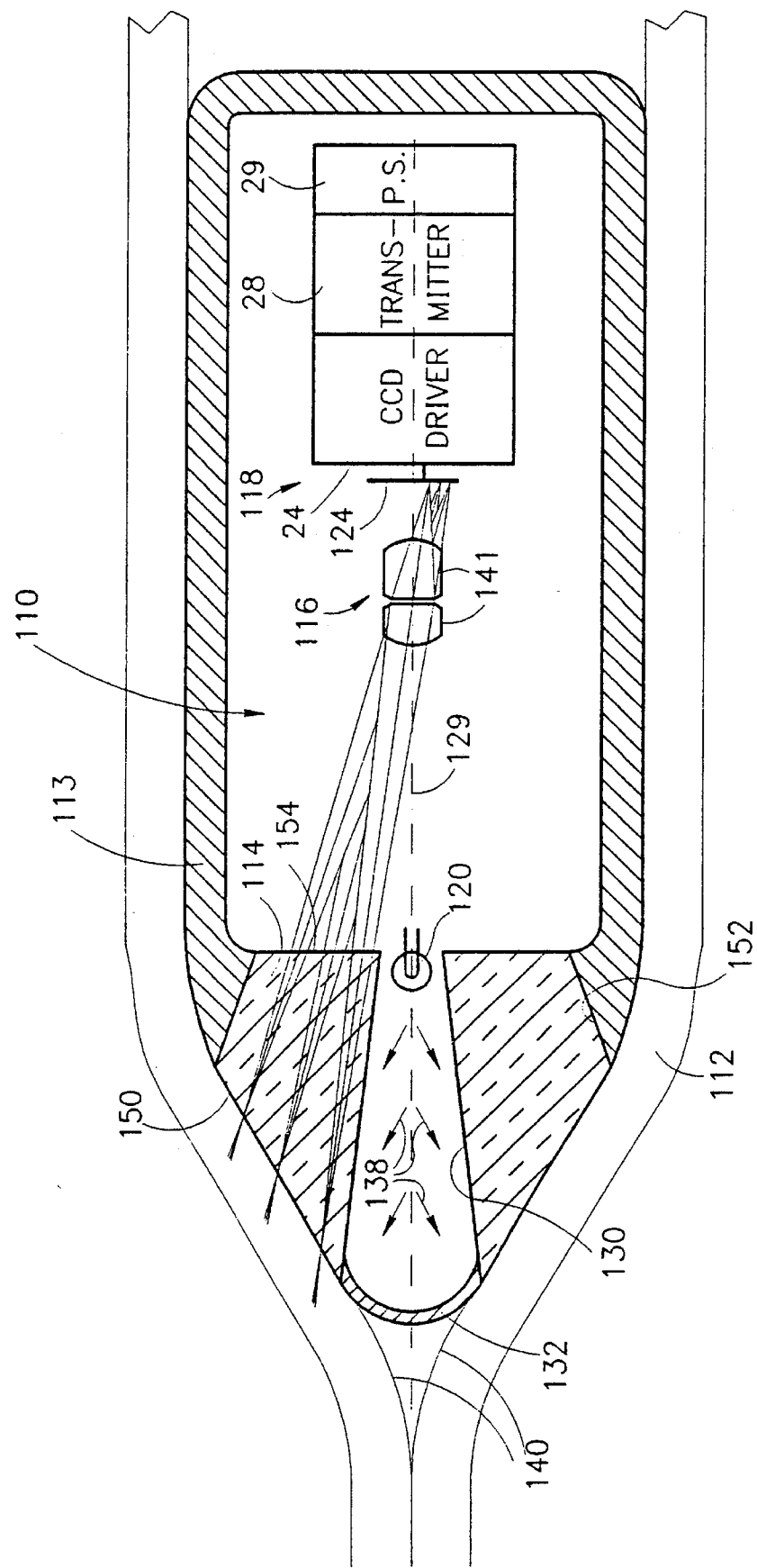
FIG. 9 is a side view illustration of an alternative embodiment of the capsule of FIG. 1 utilizing axicon optical elements.

Reference is now made to FIG. 9 which illustrates an alternative embodiment of the capsule of the present invention utilizing an axicon optical element. FIG. 9 illustrates the capsule 110 within a flexible tube 112, such as the digestive tract.

Figure 10:
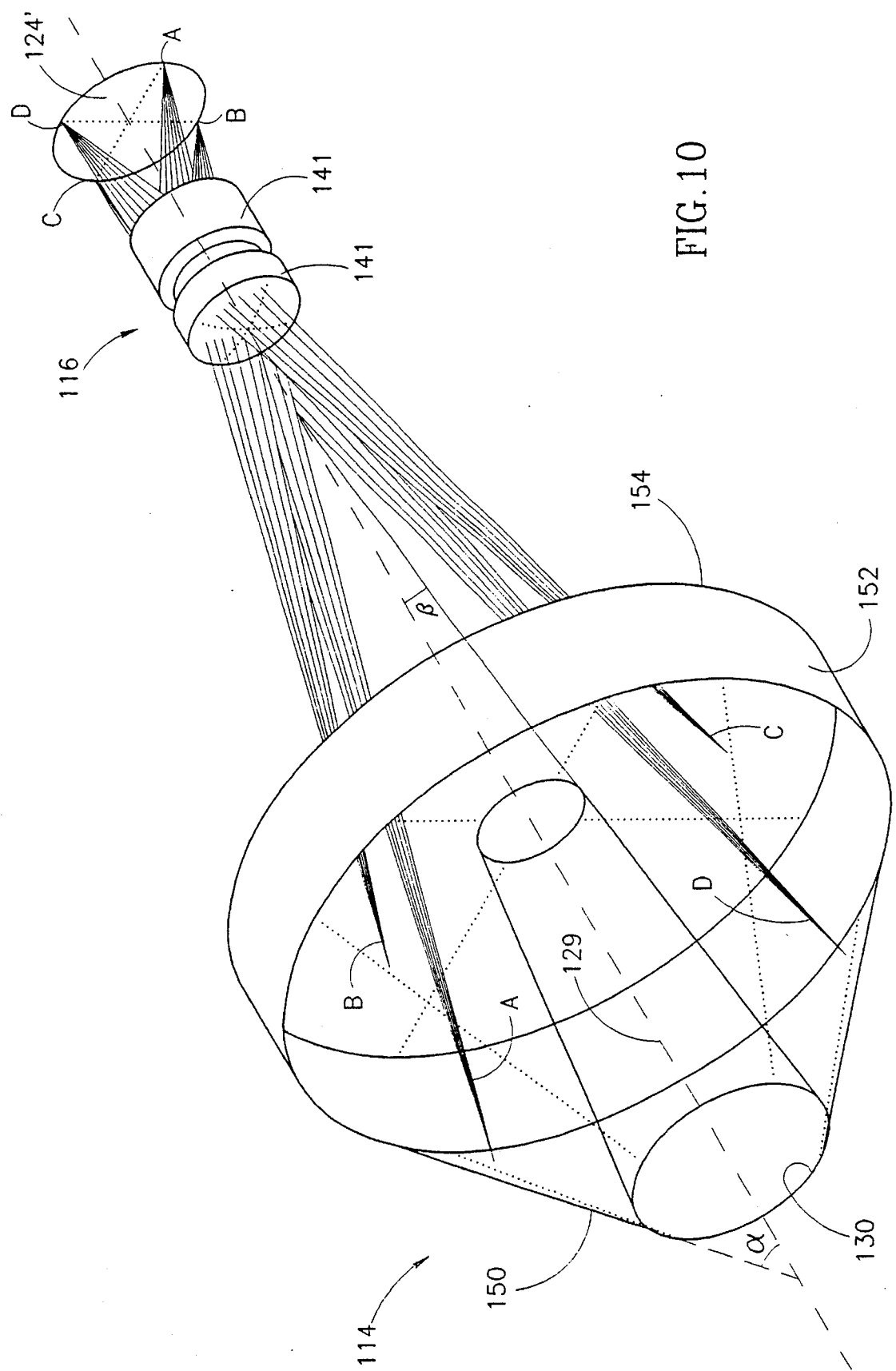
FIG. 10 is an isometric illustration of the optical paths of four light beams through the optical system of the capsule of FIG. 9.
Figure 11:
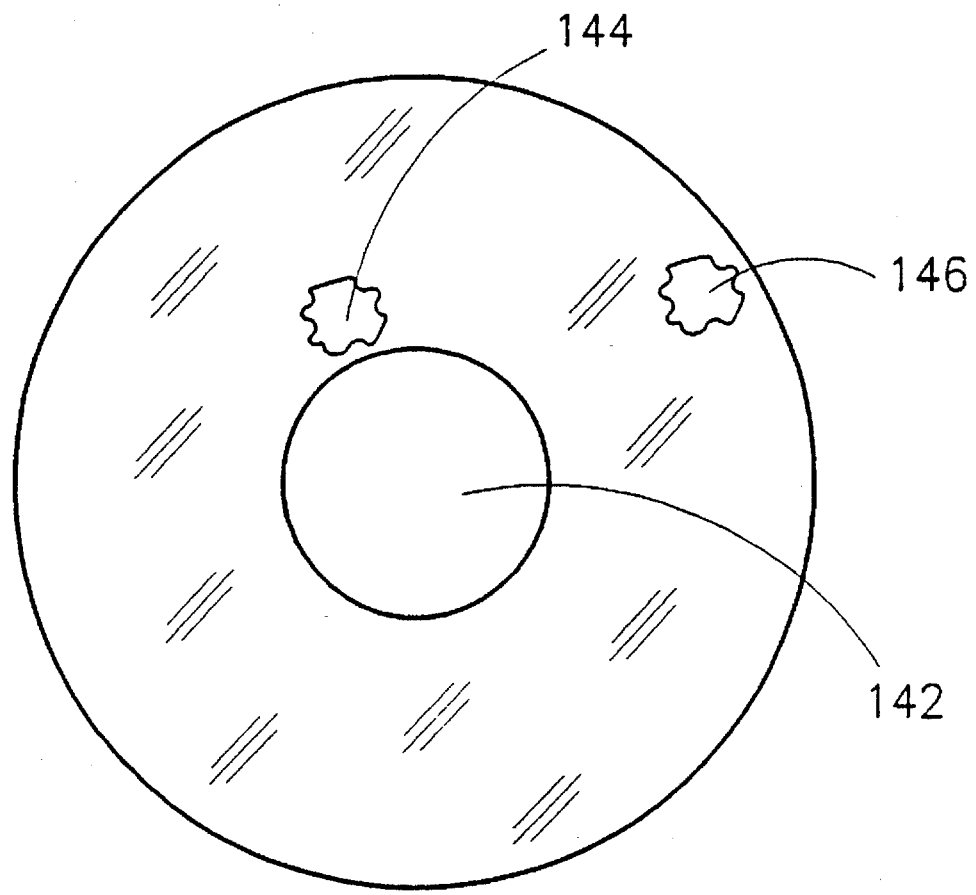
FIG. 11 is a schematic illustration of the image received at the detector plane, useful in understanding the operation of the optical system of the capsule of FIG. 9.

Reference is also made to FIGS. 10 and 11 which are useful in understanding the optics of the capsule of FIG. 9.

The capsule typically comprises a housing 113, an optical system, described in more detail hereinbelow, the transmitter 28 and the power source 29.

The optical system comprises an axicon optical element 114, which provides the angled front end, a relay lens unit 116, an image detector 118 and a light source 120. The image detector 118 is typically centered around an axis of symmetry 129 which also serves as the optical axis of the optical system. The image detector 118 typically comprises a detector 124, such as a charge coupled device (CCD), and its associated driver 126.

The axicon element 114 is the result of a rotation of a trapezoid around the axis 129. The outer sides of axicon element 114 are angled and, since axicon element 114 is the first element of the optical system to enter the digestive tract 112, axicon element 114 serves to "open up" the collapsed digestive tract 112 through which the optical system moves. As a result, the inner walls, labeled 140, of the digestive tract 112 are pressed against the outer sides of axicon element 114.

The axicon element 114 typically has a borehole 130 in the center thereof which is covered by a rounded cap 132. Axicon borehole 130 can be cylindrical or angled, as shown in the Figures.

Light source 120 is typically located within the borehole 130 and provides light to the axicon element 114. Arrows 138 indicate the directions taken by the light emitted by the light source 120. The light source 120 provides light to illuminate the inner walls 140 of digestive tract 112 which press against the axicon element 114 as the optical system of the present invention passes by. Thus, the object to be detected is present on the surface of the axicon element 114.

The objects to be detected are the inner walls 140 of a digestive tract. Due to the angled shape of the axicon element 114, the inner walls 140 are forced against the outer surface of the axicon element 114, thereby ensuring the creation of an object whose distances to the detector 124 are well defined. However, the resultant object is tilted with respect to the optical axis 129.

As is known in the art, tilted objects form images only on tilted flat detectors placed at an angle to the optical axis. This problem is known in the art as the "Scheimpflug Condition" It is discussed on pages 812–813 of the *Manual of Photogrammetry*, Vol. 1, Third Edition, American Society of Photogrammetry, 1966, which book is incorporated herein by reference. Specifically, the Scheimpflug Condition requires that the tilted object plane, the principal lens plane and the image plane must concur at a point. When imaged with conventional lenses, conical objects form conical image planes which, in turn, produce distorted and defocussed images on a flat detector.

In addition to creating the shape of the object to be detected, the axicon element 114 compensates for the conical shape of the object. This compensation is provided by the fact that the axicon element 114 is a "wedge" rather than just a conical surface. The wedge ensures that beams originating from different parts of the tilted object follow different length optical paths, the optical lengths being designed to generally compensate for the Scheimpflug Condition. Thus, the axicon element 114 produces a perpendicular object and enables the relay lens unit 116 to form an image on the detector 124 when detector 124 is perpendicular to the optical axis 129.

The relay lens unit 116 is a wide angle relay lens unit which reduces the size of the perpendicular object produced by the axicon element 114. It also serves to reduce the optical aberrations of the optical system to a minimum. As shown in FIGS. 9 and 10, the relay lens unit 116 comprises two lenses 141.

The axicon element 114 images a torus-shaped image onto detector 124. An example of such a torus-shaped detected image is illustrated in FIG. 11. The torus-shaped image has a hole 142 due to the presence of borehole 130.

In the example of FIG. 11, the blob labeled 144 is currently close to the borehole 130 and the blob labeled 146 is currently close to the outer edge of element 114. As the optical system moves further into the digestive tract 112, blob 144 moves radially toward the outer edge of the image of FIG. 11.

Axicon element 114 is typically formed of any suitable translucent material, such as glass or plastic. It has an axicon outer surface 150 (FIG. 10) having an angle α with the axis of symmetry 129, sides 152 and an inner surface 154.

The smaller the angle α is, the easier it is for the inner walls 140 to move along axicon element 114. However, if the angle α is too small, an element 114 may not be able to compensate for the Scheimpflug condition.

FIG. 10 provides a ray tracing for four beams A, B, C and D. It can be seen from the points A, B, C and D labeled on the detector plane 124', that the tilted object of the outer surface of axicon element 114 is imaged on the flat detector plane 124'. It can further be seen that axicon element 114 does not focus the image.

The following are the parameters of the optical system of the present invention for an exemplary embodiment:

Outer diameter of housing tube 113: 8 mm angle α of axicon outer surface 150: 25°–35° diameter of detector 124: 2.5–6.0 mm effective focal length of optical system: 2 mm F/# of element 114, from image side: F/2.3

Magnification: M×¼

Annular field of view: between 12° and 20°

Size of image on detector 124:
  outer diameter: 1.8 mm
  inner diameter: 0.6 mm In a further alternative embodiment of the present invention, cap 132 is formed of a lens thereby allowing imaging of the center of the digestive tract. However, this requires that the illumination come, not through the borehole, but from the side of the housing 113.

It will be appreciated by persons skilled in the art that the present invention is not limited to what has been particularly shown and described hereinabove. Rather the scope of the present invention is defined only by the claims which follow:

We claim:

1. An in vivo video camera system comprising:

a swallowable capsule comprising:

a camera system;

an optical system for imaging an area of interest onto said camera system; and a transmitter which transmits the video output of said camera system; and a reception system which receives said transmitted video output.

2. A system according to claim 1 and including means for operating said transmitter intermittently.

3. A system according to claim 1 and wherein said optical system includes a viewing window located along one side of said swallowable capsule.

4. A system according to claim 1 and wherein said reception system comprises:

an antenna array capable of surrounding a body and comprising a plurality of antennas for receiving said transmitted video output and for producing a plurality of received signals; and a demodulator capable of transforming said plurality of received video signals into a single video datastream.

5. A system according to claim 4 and also comprising a data processing system which generates tracking and video data from said single datastream.

6. A system according to claim 1 and wherein said optical system comprises:

an axicon optical element having a conical outer surface which, when said conical outer surface is in contact with inner walls of a flexible tube, creates a conical object on said conical outer surface, for compensating for the conical shape of said conical object; and a relay unit which relays said compensated object to said camara system.

7. A system according to claim 6 and wherein said axicon optical element has an axis of symmetry and a borehole centered around said axis of symmetry.

8. A system according to claim 6 and also comprising a light source located within said borehole of said axicon optical element.

9. A system according to claim 6 and wherein said axicon element is located before said relay unit and said camera system thereby to enter said flexible tube first and to open up said flexible tube if it has collapsed.

10. A reception system operable with a swallowable transmitting capsule, the reception system comprising:

an antenna array capable of surrounding a body and comprising a plurality of antennas for receiving transmitted video output from said capsule and for producing a plurality of received video signals; and a demodulator capable of transforming said plurality of received video signals into a single video datastream.

11. An autonomous video endoscope comprising:

a swallowable capsule comprising:

a camera system;

an optical system for imaging an area of interest onto said camera system; and a transmitter which transmits the video output of said camera system; and a reception system which receives said transmitted video output.

12. A system according to claim 11 and wherein said reception system comprises:

an antenna array capable of surrounding a body and comprising a plurality of antennas for receiving said transmitted video output and for producing a plurality of received signals; and a demodulator capable of transforming said plurality of received video signals into a single datastream.

13. A system according to claim 12 and also comprising a data processing system which generates tracking and video data from said single datastream.

14. A system according to claim 11 and wherein said optical system comprises:

an axicon optical element having a conical outer surface which, when said conical outer surface is in contact with inner walls of a flexible tube, creates a conical object on said conical outer surface, for compensating for the conical shape of said conical object; and a relay unit which relays said compensated object to said camara system.

15. A system according to claim 14 and wherein said axicon optical element has an axis of symmetry and a borehole centered around said axis of symmetry.

16. A system according to claim 14 and also comprising a light source located within said borehole of said axicon optical element.

17. A system according to claim 14 and wherein said axicon element is located before said relay unit and said camera system thereby to enter said flexible tube first and to open up said flexible tube if it has collapsed.

* * * * *

(12) EX PARTE REEXAMINATION CERTIFICATE (7268th)
United States Patent
Iddan et al.

(10) Number: US 5,604,531 C1
(45) Certificate Issued: Dec. 29, 2009

(54) IN VIVO VIDEO CAMERA SYSTEM

(75) Inventors: Gavriel J. Iddan, Haifa (IL); Doron Sturlesi, Timrat (IL)

(73) Assignee: Given Imaging Ltd., Yokneam (IL)

Reexamination Request:
No. 90/006,898, Dec. 30, 2003

Reexamination Certificate for:
Patent No.: 5,604,531
Issued: Feb. 18, 1997
Appl. No.: 08/374,272
Filed: Jan. 17, 1995

(30) Foreign Application Priority Data

Jan. 17, 1994 (IL) .................................................. 108352

(51) Int. Cl.
*A61B 5/07* (2006.01)
*A61B 1/05* (2006.01)

(52) U.S. Cl. ........................ 348/76; 455/100; 455/67.11; 455/67.13; 455/95; 600/109

(58) Field of Classification Search ..................... 348/76, 348/65; 455/66, 95, 100; 600/109; *H04N 7/18*
See application file for complete search history.

(56) References Cited

U.S. PATENT DOCUMENTS

| | | | |
|---|---|---|---|
| 3,683,389 A | 8/1972 | Hollis | |
| 3,971,362 A | 7/1976 | Pope et al. | |
| 4,027,510 A | 6/1977 | Hiltebrandt | |
| 4,177,800 A | 12/1979 | Enger | |
| 4,198,960 A | 4/1980 | Utsugi | |
| 4,217,045 A | 8/1980 | Ziskind | |
| 4,278,077 A | 7/1981 | Mizumoto | |
| 4,439,197 A | 3/1984 | Honda et al. | |
| 4,491,865 A | 1/1985 | Danna et al. | |
| 4,646,724 A | 3/1987 | Sato et al. | |
| 4,689,621 A | 8/1987 | Kleinberg | |
| 4,741,327 A | 5/1988 | Yabe | |
| 4,844,076 A | 7/1989 | Lesho et al. | |
| 4,917,097 A | 4/1990 | Proudian et al. | |
| 4,951,135 A | 8/1990 | Sasagawa et al. | |
| 5,010,412 A | 4/1991 | Gariss | |
| 5,042,486 A | 8/1991 | Pfeiler et al. | |
| 5,166,787 A | 11/1992 | Irion | |
| 5,187,572 A | 2/1993 | Nakamura et al. | |
| 5,222,477 A | 6/1993 | Lia | |
| 5,267,033 A | 11/1993 | Hoshino | |
| 5,273,025 A | * 12/1993 | Sakiyama et al. | ........... 600/145 |
| 5,279,607 A | 1/1994 | Schentag et al. | |
| 5,335,662 A | 8/1994 | Kimura et al. | |
| 5,368,027 A | 11/1994 | Libbers et al. | |
| 5,373,840 A | 12/1994 | Knighton | |
| 5,429,132 A | * 7/1995 | Guy et al. | .................... 600/422 |
| 5,495,114 A | 2/1996 | Adair | |
| 5,513,637 A | * 5/1996 | Twiss et al. | .................. 600/424 |
| 5,603,687 A | 2/1997 | Hori et al. | |
| 5,662,587 A | 9/1997 | Grundfest et al. | |
| 5,819,736 A | 10/1998 | Avny et al. | |

FOREIGN PATENT DOCUMENTS

| | | |
|---|---|---|
| DE | 29 29 429 | 2/1980 |
| DE | 34 40 177 | 5/1986 |
| JP | 57-45833 | 3/1982 |
| JP | HEI 3-289779 | 12/1991 |
| JP | HEI 4-109927 | 4/1992 |
| JP | 04-144533 | 5/1992 |

(Continued)

OTHER PUBLICATIONS

Rowlands, et al., "The Radio Pill: Telemetering from the Digestive Tract", British Communications and Electronics, Aug. 1960, pp. 598–601.

(Continued)

*Primary Examiner*—Ovidio Escalante

(57) ABSTRACT

An in vivo video camera system and an autonomous video endoscope are described. Each system includes a swallowable capsule, a transmitter and a reception system. The swallowable capsule includes a camera system and an optical system for imaging an area of interest onto the camera system. The transmitter transmits the video output of the camera system and the reception system receives the transmitted video output.

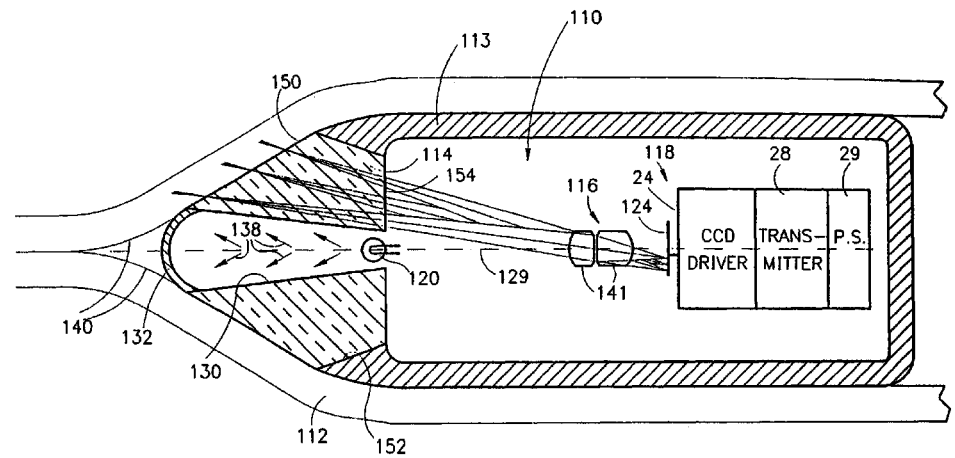

FOREIGN PATENT DOCUMENTS

| | | |
|---|---|---|
| JP | 4144533 | 5/1992 |
| JP | HEI 4-180736 | 6/1992 |
| JP | 5015515 | 1/1993 |
| JP | 6114037 | 4/1994 |
| JP | 6142081 | 5/1994 |
| JP | 6285044 | 10/1994 |
| JP | 111985 | 5/1995 |
| WO | WO 92/21307 | 12/1992 |
| WO | WO 94/05200 | 3/1994 |

OTHER PUBLICATIONS

Yarborough, III et al., "Evaluation of the Heidelberg pH Capsule: Method of Tubeless Gastric Analysis", The American Journal of Surgery, vol. 117, Feb. 1969, pp. 185–192.

Bio–Medical Telemetry: "Sensing and Transmitting Biological Information from Animals and Man", R. Stuart Mackay, John Wiley and Sons, New York, 1970, pp. 244–245.

"Manual of Photogrammety", vol. II, Third Edition, American Society of Photogrammetry, 1966, pp. 812–813.

H. Lange et al. "Heidelberger Kapsel—ein Kleinststender fur die pH–Messung im Magen", Telefunk–Zeitung, vol. 36, No. 5, 1963, pp. 265–270.

"Studies of the Human Gastro–Intestinal Tract in the Ambulatory Subject Using the Pressure Sensitive Radiotelemetry Capsule", Evans et al., Proc. Int. Symp. on Ambulatory Monitoring, 1980, pp. 415–421.

"Diagnostic Imaging in 3 Easy Steps", date unknown.

"The Heidelburg pH Capsule System Telemetric Fasting Gastric Analysis", date unknown.

European Search Report of European Application No. EP 95 30 0254, commonly owned by assignee of patent under reexamination, dated Jun. 7, 1995.

Expert Report of Rodney Vaughan, Ph.D., Civil Action No. 08 CV 02132 (JKG) (HSP) dated Feb. 26, 2008.

Lange, H. and Noeller G. "The Heidelberg Capsule—A Micro–Transmitter for Measuring Stomach pH" Telefunken Zeitung, vol. 36, Issue 5, 1963, pp. 265–271.

Masaharu Hata and Takayoshi Nagatsu "Mobile Location Using Signal Strength Measurements in a Cellular System" IEEE Transactions on Vehicular Technology, vol. VT–29, No. 2, May 1980, pp. 245–252.

Rebuttal Expert Report of Dr. John Grindon Concerning Validity of the 531 Patents—Redacted, Civil Action No. 06 CV 02132 (JKG) (HSP), dated Mar. 25, 2008.

Rebuttal Expert Report of Duncan T. Moore, Ph.D.—Redacted, Civil Action No. 06 CV 02132 (JKG)(HSP), dated Mar. 25, 2008.

William G. Figel, Neal H. Shepherd and Walter F. Trammell "Vehicle Location by a Signal Attenuation Method" IEEE Transactions on Vehicular Technology, vol. VT–18, No. 3, Nov. 1969.

Expert Report of Dr. Dennis C. Leiner—Redacted, Civil Action No. 06 CV 02132 (JKG)(HSP), dated Feb. 26, 2008.

* cited by examiner

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, lines 32–40:

The antenna array 40 typically comprises a multiplicity of antennas 44, each formed of a rectangular or circular coil of wire, held within a suitably insulating material, such as cloth or plastic. In the exemplary embodiment illustrated in FIG. 4, there are shown 16 antennas [42] *44*, formed into two rows of eight antennas [42] *44* each. Fewer or more antennas can be utilized as long as they are located so as to be able to determine from their output the location of the capsule 10 within the body of the patient.

Column 4, lines 41–47:

The signal sampler 42 typically comprises a multiplicity of receivers 46 (FIG. [3] *5*), one for each antenna 44 and connected thereto with a thin coaxial cable 47, and a multiplexer 48. The receivers 46 decipher the data provided by their corresponding antennas 44. The multiplexer 48 continually scans the output of the receivers 46, providing the combined antenna data as a single output signal.

AS A RESULT OF REEXAMINATION, IT HAS BEEN DETERMINED THAT:

The patentability of claims 4, 5, 10, 12–13, 16 and 17 is confirmed.

Claims 1–3 and 11 are cancelled.

Claims 6 and 14 are determined to be patentable as amended.

Claims 7–9 and 15, dependent on an amended claim, are determined to be patentable.

6. A system according to claim 1 and wherein said optical system comprises:
an axicon optical element having a conical outer surface which, when said conical outer surface is in contact with inner walls of a flexible tube, creates a conical object on said conical outer surface, for compensating for the conical shape of said conical object; and
a relay unit which relays said compensated object to said [camara] *camera* system.

14. A system according to claim 11 and wherein said optical system comprises:
an axicon optical element having a conical outer surface which, when said conical outer surface is in contact with inner walls of a flexible tube, creates a conical object on said conical outer surface, for compensating for the conical shape of said conical object; and
a relay unit which relays said compensated object to said [camara] *camera* system.

\* \* \* \* \*